US007575877B2

(12) United States Patent
Hasnain et al.

(10) Patent No.: US 7,575,877 B2
(45) Date of Patent: Aug. 18, 2009

(54) METHOD OF DIAGNOSING TUBERCULOSIS (75) Inventors: Seyed Ehtesham Hasnain, Hyderabad (IN); Sharmistha Banerjee, Hyderabad (IN); Ashok Nandyala, Hyderabad (IN); Raviprasad Podili, Hyderabad (IN); Vishaw M Katoch, Agra (IN); Kolluri Janaki Rama Murthy, Hyderabad (IN)

(73) Assignee: Centre for DNA Fingerprinting and Diagnostics, Department of Biotechnology, Ministry of Science & Technology, Government of India. Nacharam., Hyderabad (IN)

( * ) Notice: Subject to any disclaimer, the term of this patent is extended or adjusted under 35 U.S.C. 154(b) by 0 days.

(21) Appl. No.: 11/572,222

(22) PCT Filed: Jul. 20, 2005

(86) PCT No.: PCT/IN2005/000245

§ 371 (c)(1),
(2), (4) Date: Nov. 14, 2007

(87) PCT Pub. No.: WO2006/008760

PCT Pub. Date: Jan. 26, 2006

(65) Prior Publication Data

US 2008/0064051 A1 Mar. 13, 2008

(30) Foreign Application Priority Data

Jul. 21, 2004 (IN) .......................... 710/CHE/2004

(51) Int. Cl.
G01N 33/53 (2006.01)
A61K 39/04 (2006.01)
(52) U.S. Cl. ............................. 435/7.1; 435/7.2; 435/4; 436/501; 436/513; 424/9.1; 424/9.2; 424/130.1; 424/164.1; 424/184.1; 424/234.1; 424/248.1
(58) Field of Classification Search .................. 424/9.1, 424/9.2, 184.1, 234.1, 248.1, 130.1, 164.1; 435/4, 7.1, 7.2; 436/501, 513
See application file for complete search history.

(56) References Cited

OTHER PUBLICATIONS

Ohman, R., et al. Purification and characterisation of isocitrate dehydrogenase and malate dehydrogenase from *Mycobacterium tuberculosis* and evaluation of their potential as suitable antigens for the serodiagnosis of tuberculosis. Tubercle and Lung Disease, vol. 77, pp. 454-461, 1996.*
Mackie, T.J., "*Mycobacterium*: tubercle bacilli", Mackie & McCartney Practical Medical Microbiology, 1989, pp. 399-416, vol. QR46.M35.
Andersen, Peter et al., "Proteins Released From *Mycobacterium tuberculosis* During Growth", Infection and Immunity, Jun. 1991, pp. 1905-1910, vol. 59, No. 7, American Society for Microbiology.
Perschinka, Hannes et al., "Cross-Reactive B-Cell Epitopes of Microbial and Human Heat Shock Protein 60/65 in Atherosclerosis", Arterioscler Thromb Vasc Biology, 2003, pp. 1060-1065, American Heart Association.
Hadad, D.J. et al., "Mycobacteraemia among HIV-1-Infected Patients in Sao Paulo, Brazil: 1995 to 1998", Epidemiol Infect, 2003, pp. 151-155, Cambridge University Press.
Saiman, Lisa, "The Mycobacteriology of Non-Tuberculous Mycobacteria", Paediatric Respiratory Reviews, 2004, 3 pages, Elsevier Science Ltd.
Siddiqi, Noman et al., "Molecular Characterization of Multidrug-Resistant Isolates of *Mycobacterium tuberculosis* From Patients in North India", Antimicrobial Agents and Chemotherapy, Feb. 2002, pp. 443-450, vol. 46, No. 2, American Society for Microbiology.
Chakhaiyar, Prachee et al., "Defining the Mandate of Tuberculosis Research in a Postgenomic Era", Karger, 2004, pp. 177-184, Karger AG, Basel.
Perkins, Mark D. et al., "Serologic Diagnosis of Tuberculosis Using a Simple Commercial Multiantigen Assay", Chestjournal, Jan. 2003, 8 pages, American College of Chest Physicians.
Ramalingam, B. et al., "Isotype-Specific Anti-38 and 27 kDa (mpt 51) Response in Pulmonary Tuberculosis with Human Immunodeficiency Virus Coinfection", Taylor & Francis Health Sciences, 2003, pp. 234-239.
Dye, Christopher et al., "Global Burden of Tuberculosis, Estimated Incidence, Prevalence, and Mortality by Country", American Medical Association, 1999, pp. 677-686, vol. 282, No. 7, JAMA.
Horwitz, Marcus A. et al., "Protective Immunity Against Tuberculosis Induced By Vaccination With Major Extracellular Proteins of *Mycobacterium tuberculosis*", Proc. Natl. Acad. Sci., Feb. 1995, pp. 1530-1534, vol. 92.
Trajkovic, Vladimir et al., "Immunomodulatory Action of Mycobacterial Secretory Proteins", Microbes and Infections, 2004, pp. 513-519, Elsevier SAS.
Ridell, R. Ohman M., "Purification and Characterisation of Isocitrate Dehydrogenase and Malate Dehydrogenase From *Mycobacterium tuberculosis* and Evaluation of Their Potential as Suitable Antigens for the Serodiagnosis of Tuberculosis", Tubercle and Lung Disease, 1996, pp. 454-461, Pearson Professional Ltd.
Bradford, Marion M., "A Rapid and Sensitive Method for the Quantitation of Microgram Quantities of Protein Utilizing the Principle of Protein-Dye Binding", Analytical Biochemistry, 1976, pp. 248-254, Academic Press, Inc.
Shiratsuch, Hiroe et al., "Caspase Activation May Be Associated With *Mycobacterium avium* Pathogenicity", The American Journal of Surgery, 2003, pp. 547-551, Excerpta Medica, Inc.
Ahmed, Niyaz et al., "Molecular Genotyping of a Large, Multicentric Collection of Tubercle Bacilli Indicates Geographical Partitioning of Strain Variation and Has Implications for Global Epidemiology of *Mycobacterium tuberculosis*", Journal of Clinical Microbiology, Jul. 2004, pp. 3240-3247, American Society for Microbiology.
Dye, Christopher et al., "Worldwide Incidence of Multidrug-Resistant Tuberculosis", The Journal of Infectious Diseases, 2002, pp. 1197-1202.

(Continued)

*Primary Examiner*—Rodney P. Swartz
(74) *Attorney, Agent, or Firm*—Vern Maine & Associates (57) ABSTRACT

The present invention relates to a method of diagnosing tuberculosis in a subject, said method comprising steps of: detecting anti-*Mycobacterium tuberculosis* (M.tb.) isocitrate dehydrogenase (ICDs) antibody in the subject, and diagnosing tuberculosis in the subject.

3 Claims, 4 Drawing Sheets

OTHER PUBLICATIONS

Chakhaiyar, Prachee et al., "Regions of High Antigenicity Within the Hypothetical PPE Major Polymorphic Tandem Repeat Open-Reading Frame, Rv2608, Show a Differential Humoral Response and a Low T Cell Response in Various Categories of Patients with Tuberculosis", The Journal of Infectious Diseases, 2004, pp. 1237-1244, The Infectious Diseases Society of America.

Maekura, Ryoji et al., "Prospective Clinical Evaluation of the Serologic Tuberculous Glycolipid Test in Combination with the Nucleic Acid Amplification Test", Journal of Clinical Microbiology, Mar. 2003, pp. 1322-1325, vol. 41, No. 3, American Society for Microbiology.

Bloom, Barry R. et al., "Tuberculosis: Commentary On A Reemergent Killer", Science, Aug. 21, 1992, pp. 1055-1064, vol. 257.

Mustafa, Abu Salim, "Development of New Vaccines and Diagnostic Reagents Against Tuberculosis", Molecular Immunology, 2002, pp. 113-119, Elsevier Science Ltd.

Mori, Toru et al., "Specific Detection of Tuberculosis Infection, An Interferon-γ-Based Assay Using New Antigens", American Journal of Respiratory and Critical Care Medicine, 2004, pp. 59-64, vol. 170.

Florio, W. et al., "Identification, Molecular Cloning, and Evaluation of Potential Use of Isocitrate Dehydrogenase II of *Mycobacterium bovis* BCG in Serodiagnosis of Tuberculosis", Clinical and Diagnostic Laboratory Immunology, Jul. 2002, pp. 846-851, vol. 9, No. 4, American Society for Microbiology.

Choudhary, Rakesh Kumar et al., "PPE Antigen Rv2430c of *Mycobacterium tuberculosis* Induces a Strong B-Cell Response", Infection and Immunity, Nov. 2003, pp. 6338-6343, vol. 71, No. 11, American Society for Microbiology.

Bardou, Fabienne et al., "Effects of Isoniazid on Ultrastructure of *Mycobacterium aurum* and *Mycobacterium tuberculosis* and on Production of Secreted Proteins", Antimicrobial Agents and Chemotherapy, Nov. 1996, pp. 2459-2467, vol. 40, No. 11, American Society for Microbiology.

Ahmed, Niyaz et al., "Distintiveness of *Mycobacterium tuberculosis* Genotypes From Human Immunodeficiency Virus Type 1-Seropositive and -Seronegative Patients in Lima, Peru", Journal of Clinical Microbiology, Apr. 2003, pp. 1712-1716, vol. 41, No. 4, American Society for Microbiology.

Maekura, Ryoji et al., "Clinical Evaluation of Anti-Tuberculosis Glycolipid Immunoglobulin G Antibody Assay for Rapid Serodiagnosis of Pulmonary Tuberculosis", Journal of Clinical Microbiology, Oct. 2001, pp. 3603-3608, vol. 39, No. 10, American Society for Microbiology.

Brusasca, Pier Natale et al., "Antigen Recognition by Serum Antibodies in Non-Human Primates Experimentally Infected with *Mycobacterium tuberculosis*", Comparative Medicine, 2003, pp. 165-172, vol. 53, No. 2, American Association for Laboratory Animal Science.

Helmuth, Laura, "A Weak Link in TB Bacterium is Found", Science, Aug. 2000, pp. 1123-1125, vol. 289, No. 5482.

Skjøt, Rikke Louise Vinther et al., "Antigen Discovery and Tuberculosis Vaccine Development in the Post-Genomic Era" Scand J Infect Dis, 2001, pp. 643-647, Taylor & Francis.

Roche, PW et al., "Differential T Cell Responses to Mycobacteria-Secreted Proteins Distinguish Vaccination with Bacille Calmette-Guérin From Infection with *Mycobacterium tuberculosis*", J Infec Dis., Nov. 1994, pp. 1326-1330, vol. 170, No. 5, Centenary Institute of Cancer Medicine and Cell Biology, Newton, Australia.

\* cited by examiner

SEQUENCE LISTING

<160> NUMBER OF SEQ ID NOS: 4

<210> SEQ ID NO 1
<211> LENGTH: 27
<212> TYPE: DNA
<213> ORGANISM: Mycobacterium tuberculosis

<400> SEQUENCE: 1
ggatccatgt ccaacgcacc caagata            27

<210> SEQ ID NO 2
<211> LENGTH: 27
<212> TYPE: DNA
<213> ORGANISM: Mycobacterium tuberculosis

<400> SEQUENCE: 2
aagcttctaa ttggccagct cctttc            27

<210> SEQ ID NO 3
<211> LENGTH: 28
<212> TYPE: DNA
<213> ORGANISM: Mycobacterium tuberculosis

<400> SEQUENCE: 3
agcttggatc catgagcgcc gaacagcc            28

<210> SEQ ID NO 4
<211> LENGTH: 28
<212> TYPE: DNA
<213> ORGANISM: Mycobacterium tuberculosis

<400> SEQUENCE: 4
catggaagct ttcagccttg gacagcct            28

METHOD OF DIAGNOSING TUBERCULOSIS

RELATED APPLICATIONS

The present national phase application of a PCT application claims the benefit of Indian Patent Application No. 710/CHE/2004 dated Jul. 21, 2004. The application is herein incorporated in its entirety by reference.

FIELD OF THE INVENTION

Introduction

Tuberculosis, caused by *Mycobacterium tuberculosis*, remains a major threat to human population, roughly responsible for 2-3 million deaths every year worldwide (1-3). The secret of the pathogen's success is its ability to escape the host immune system and remain undetected in lungs for decades. Only in 10% of the infected people, the number being higher in immuno-compromised patients, TB erupts as a full-blown disease (4). Delay in diagnosis and treatment impedes the downstream management and control of the disease. With the increasing emergence of multi drug resistant strains and co-infection with HIV the problem is getting further compounded (5-7). Early diagnosis, therefore, is a matter of utmost concern not just for TB disease management but also for epidemiological investigations (8). Current diagnostic tools for tuberculosis often lack sensitivity and can be time consuming. TB diagnosis in developing countries largely banks upon tuberculin skin test and staining and culture methods. The epidemiological relevance of tuberculin test with purified protein derivative (PPD) is questionable in areas where BCG vaccination is compulsory because PPD is not sensitive enough to distinguish between vaccinated and infected individuals (9). Microscopic determination of the *bacilli* in the sputum samples is a direct way of examining pulmonary tuberculosis (5). This however requires high titers of *bacilli* (5000-10000/ml) in sputum—a condition seen only in full blown tuberculosis patients. Culture techniques can detect very low titers but are time consuming taking approximately 3-6 weeks (10).

The importance of the major extracellular proteins of the pathogen as candidate components of a subunit vaccine has been reported earlier (11). Current discovery of the RD1 locus in the Mtb genome, encoding mainly the proteins actively secreted by *mycobacteria* into the culture medium, such as CFP-10 and ESAT-6, have further encouraged immunological tests as an adjunct to conventional diagnosis (12-15). Proteins that are released from *Mycobacterium tuberculosis* during late logarithmic growth phase, such as superoxide dismutase and isocitrate dehydrogenase are employed as autolysis markers (16). The use of isocitrate dehydrogenase as a potential antigen for serodiagnosis along with malate dehydrogenase has been suggested (17, 18). The *Mycobacterium tuberculosis* genome carries two isoforms of isocitrate dehydrogenase, M.tb ICD-1 and M.tb ICD-2. Multiple sequence alignment revealed a closer similarity of M.tb ICD-1 to eukaryotic NADP.sup.+ dependent ICDs, while M.tb ICD-2 groups with bacterial ICDs. We have evaluated the utility of ICDs as immunogenic markers for tuberculosis through detection of anti-M.tb ICD antibody in sera of different well characterized categories of TB patients through enzyme linked immunosorbent assays. We describe the sensitivity and specificity of ICDs to distinguish TB patients from those vaccinated with BCG, and also from those patients infected with non-tuberculous *mycobacteria* or other pathogens vis-a-vis the conventional antigen-HSP 60 (19) and purified protein derivative (PPD).

BRIEF DESCRIPTION OF THE SEVERAL VIEWS OF THE DRAWINGS

Table 1 presents PCR primers and thermal cycle parameters for amplification of M.tb ICD-1 and ICD-2 in accordance with one embodiment of the present invention.

MATERIALS AND METHODS

Cloning, Expression and Purification of M.tb ICD-1 and M.tb ICD-2: The ORFs, corresponding to M.tb ICD-1 (Rv3339c, 1.230 kb) and M.tb ICD-2 (Rv0066c, 2.238 kb) were PCR amplified from the genomic DNA of H37Rv. BamHI and HindII restriction sites were incorporated in the 5' end of forward and reverse primers respectively for both M.tb ICD-1 and M.tb ICD-2. The primers and parameters for thermal cycle amplification have been tabulated in table 1. The amplicons carring the full length M.tb ICD-1 and M.tb ICD-2 were cloned at the BamHI HindIII sites of the expression vector pRSET-A (Invitrogen, USA) with six histidine sequence tag at N-terminel. The generated constructs 'setAicd1' and 'setAicd2' were further transformed into the BL21 (DE3) strain of *E.coli*. The clones were confirmed by sequencing using the T7 promoter primer, on an ABI prism 377 DNA sequencer (PE Biosystems, USA).

Figure 1:
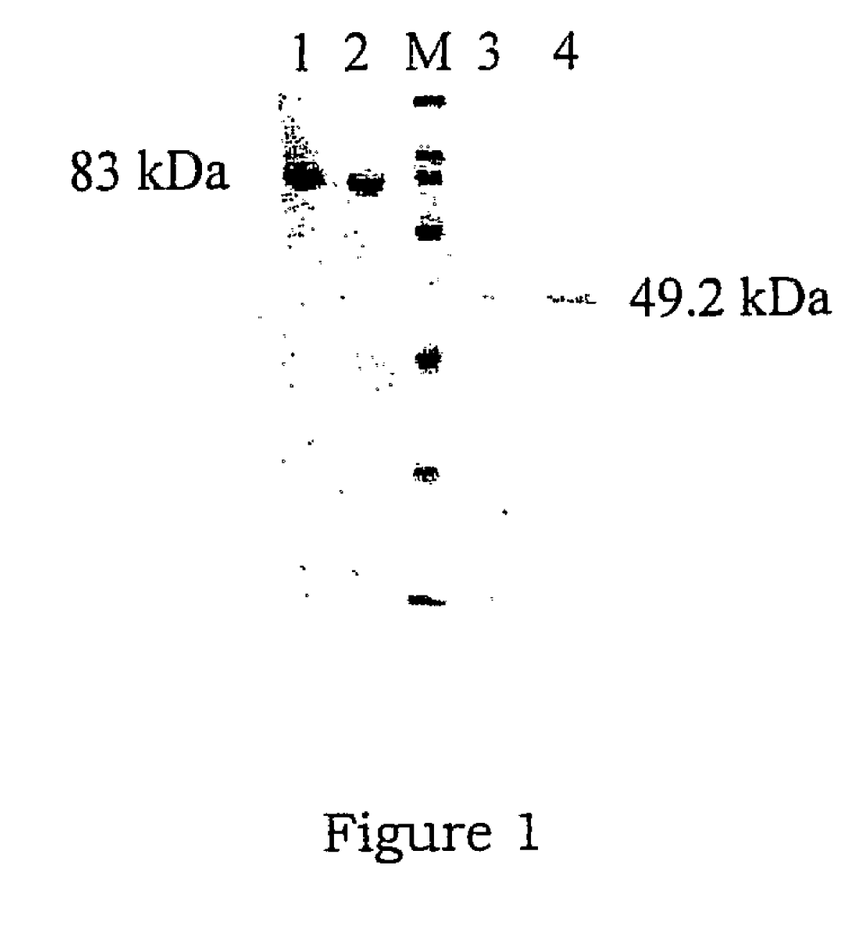
FIG. 1 depicts absorbance values at 492 nm for affinity purification of M.tb ICD-1 and M.tb ICD-2 in accordance with one embodiment of the present invention.

The genes were over-expressed in the pRSET-A/ *E.coli* BL-21 (DE3) expression system. The over-expressed his-tagged recombinant protein was purified by $Ni^{2+}$-nitrilotriacetate affinity chromatography. The cells transformed with the constructs were grown in Terrific Broth (TB) containing ampicillin (100 µg/ml) to an $OD_{600}$ of 0.4 to 0.5 at 37° C., cooled to 27° C. induced with 0.1 mM isopropyl β-D-thiogalactoside and grown overnight at 27° C. The cells were lysed by sonication, followed by centrifuging at 13000 rpm for 30 minutes at 4° C. The clear lysate was loaded onto $Ni^{2+-NTA}$ column, which was then washed with 50 mM $NaH_2PO_4$, 300 mM NaCl, 20 mM imidazole, pH 8. The proteins was eluted in the same buffer supplemented with 200 mM imidazole. The proteins were 90-95% pure as seen on 10% SDS-PAGE followed by Commasie Blue staining (FIG. 1). The purified recombinant proteins were dialyzed against 20 mM TrisCl, pH7.5 with 100 mM NaCl and 3% glycerol and quantified using Bradford Reagent (20).

Human Sera: The study population (n=215) was comprised of the M.tb infected human sample population reporting to Mahavir Hospital and Research Centre, Hyderabad and Central JALMA Institute for Leprosy, Agra. These were categorized into three groups, namely group 1 (n=42 patients), group 2 (n=32 patients) and group 3 (n=35 patients). In addition to the above 44 clinically healthy donors, 30 NTM cases and 32 non-TB patients who were proven culture negative for acid fast bacteria were also included as controls in this study. Group 1 was comprised of patients with fresh infection with no history of TB treatment. Group 2 was comprised of patients with relapsed cases, i.e. those who were treated earlier for tuberculosis but the symptoms re-emerged after the completion of the treatment. Group 3 included patients with extra-pulmonary tuberculosis. Group 1 and group 2 patients were diagnosed by sputum examination (acid-fast *bacillus* smear positive and negative) while the extra-pulmonary cases were confirmed by tissue biopsy. Clinically healthy donors were *M. bovis* BCG vaccinated and had no symptoms of TB at the time of sera collection. Randomly picked individuals from the population of healthy controls were subjected to PCR test for TB and were found to be PCR negative. *Mycobacteria* other than *M. leprae* that are not included in the *M. tuberculosis* complex are referred to as nontuberculous *mycobacteria* or NTM (21). However, the group referred to as NTMs in this study included sera collected from patients infected with non-tuberculous mycobacterial species (n=14), such as, *M. avium, M. xenopi*, and *M. fortuitum* as well as sera from patients with *M. leprae* infection (n=16). The non-TB patient category included infected individuals who were tested negative for acid fast bacteria by staining and culture based techniques. These patients were also negative for HIV and HBV. These randomly picked patients were suffering from either pneumonia, lower respiratory infections, septic emia, urinary tract infections, gastrointestinal infections, cirrhosis or fever of unknown origin. The study population had no sex or age bias. This study was approved by the Institutional Ethics Committee.

Immunosorbent assays: Enzyme linked immunosorbent assays (ELISA) were performed to check the B cell immune response in human to the M. tb ICD-1 and ICD-2 proteins and control antigen HSP 60 and PPD. HSP 60 used was M. tb HSP65/GroEL. In brief, the 96 well microtitre plates (Corning, Costar, USA) were coated with ~500 ng of either control antigens or recombinant M.tb ICD-1 and M.tb ICD-2. The plates were incubated overnight at 4° C., washed thrice with phosphate buffer saline (PBS) and blocked with 100 µl of blocking buffer (2% BSA in PBS) for 2 hour at 37° C. The plates were then washed thrice with wash buffer PBST (0.05% Tween 20 in 1 X PBS). The *M. tuberculosis* infected human sera belonging to different clinical groups were diluted 200times in blocking buffer (1% BSA in PBS). 50 µl of sera were added to antigen coated wells followed by incubation for 1 hr at 37° C. The plates were thoroughly washed with PBST and further incubated with anti-human IgG-horseradish peroxidase (HRP) (Sigma, USA) at 37° C. for 1hr. HRP activity was detected using a chromogenic substance o-phenylenediamine tetrahydrochloride (Sigma, USA) in citrate-phosphate buffer (pH 5.4) and (Qualigens, India) as 1 µl/ml. The reactions were terminated using 1N $H_2SO_4$, and the absorbance values were measured at 492 nm in an ELISA reader (BioRad, USA). Each ELISA was repeated at least twice with some randomly picked sera samples tested thrice for confirmation, with and without replicates for each sample within individual ELISA.

Data analysis: t-test was performed to compare the means of two variable groups, healthy and infected classes, using the online scientific calculator of GraphPad, the quickcalcs ttest1.cfm file, to calculate means, standard error of means (SEM) and p values.

RESULTS

Expression and purification of M.tb ICD-1 and M.tb ICD-2

The over-expressed N-terminal His-tagged M.tb ICD-1 was purified to 95% homogeneity on a Nickel affinity column (FIG. 1). The molecular size of the recombinant ICD-1 was determined to be 49.2 kDa. The purification was carried out under native conditions from soluble fraction with an yield of 3.25 mg protein per 500 ml of start culture. Similarly M.tb ICD-2, a 83 kDa protein, was purified to 90-95% homogeneity (FIG. 1) with an yield of about 20.4 mg per 1000 ml of start culture.

M.tb ICD-1 and M.tb ICD-2 Show High Reactivity to Patient Sera as Opposed to BCG-Vaccinated Healthy Controls Humoral immune responses directed against the M.tb ICD-1 and M.tb ICD-2 were compared between patients with tuberculosis and BCG-vaccinated healthy controls (FIGS. 2A and 2B). The recombinant proteins were used to screen the infected and the healthy sera by ELISA using anti-human IgG-HRP as conjugates. The sera were also tested against M.tb HSO 60 and the purified protein derivative (PPD) (FIGS. 2C and 2D). The immunoreactivity of ICD-1, ICD-2, HSP 60 and PPD were statistically analysed and compared with respect to both infected and healthy sera. These data demonstrate that sera of all the infected patients mounted a statistically significant ($p<0.0001$) antibody response against recombinant M.tb ICD-1 and M.tb ICD-2 proteins as compared to that of the healthy controls. PPD, on the other hand, reacted against both healthy as well as TB infected sera. It is interesting to note that as compared to ICD-1 and ICD-2 ($p<0.0001$) the difference in the reactivity of PPD to total infected and healthy sera was negligible and statistically insignificant ($p=0.2301$). Since PPD, a mixture of proteins, showed statistically insignificant discrimination between healthy and different categories of infected population (FIG. 2D), the reactivities of the recombinant proteins were compared with the B-cell response to M.tb HSP 60 (FIG. 2C) in different categories of patients. The difference between reactivity to HSP 60 between TB patients and healthy controls was statistically not quite significant ($p=0.0645$).

A correlation between reactivity against M.tb ICD-1 and M.tb ICD-2 in patient sera with the state of disease, fresh or relapse, was attempted by comparing the antibody responses to M.tb ICD-1 and M.tb ICD-2 between various clinical categories (FIGS. 2A and 2B respectively). M.tb ICD-1 failed to discriminate between fresh, relapsed and extra-pulmonary TB cases as no significant differences in immunoreactivity in different patient groups were observed (FIG. 2A). Yet as compared to BCG-vaccinated healthy controls, each category yielded p values less than 0.0001 indicating that M.tb ICD-1 can differentiate substantially between BCG-vaccinated healthy population and any category of M.tb infected patients, pulmonary or non-pulmonary. M.tb ICD-2, on the other hand, could also discriminate relapsed cases from both fresh infections ($p<0.0001$) and extrapulmonary infections ($p=0.0003$). Like M.tb ICD-1, M.tb ICD-2 could also distinguish substantially between BCG-vaccinated healthy population and any category of M.tb infected patients. Surprisingly, HSP 60, even though it could discriminate Group 1 and Group 2 from healthy controls ($p=0.0011$ and 0.0036 respectively), failed to distinguish the extrapulmonary infections from BCG vaccinated healthy controls ($p=0.2177$). These results demonstrate that (i) recombinant M.tb ICD-1 and ICD-2 proteins could differentiate sera from TB infected patients vis-a-vis healthy BCG vaccinated controls, (ii) the extrapulmonary infections that could not be distinguished from healthy controls by HSP 60, could be significantly identified and categorized by M.tb ICDs and (iii) M.tb ICD-2 mounted a stronger antibody response in relapsed cases and could significantly discriminate them from Group 1 and Group 3 categories. These proteins, which have an apparently important metabolic role, are thus able to elicit a strong B-cell response as a function of the TB infection.

Immunodominace of ICDs Over HSP 60

Figure 3:
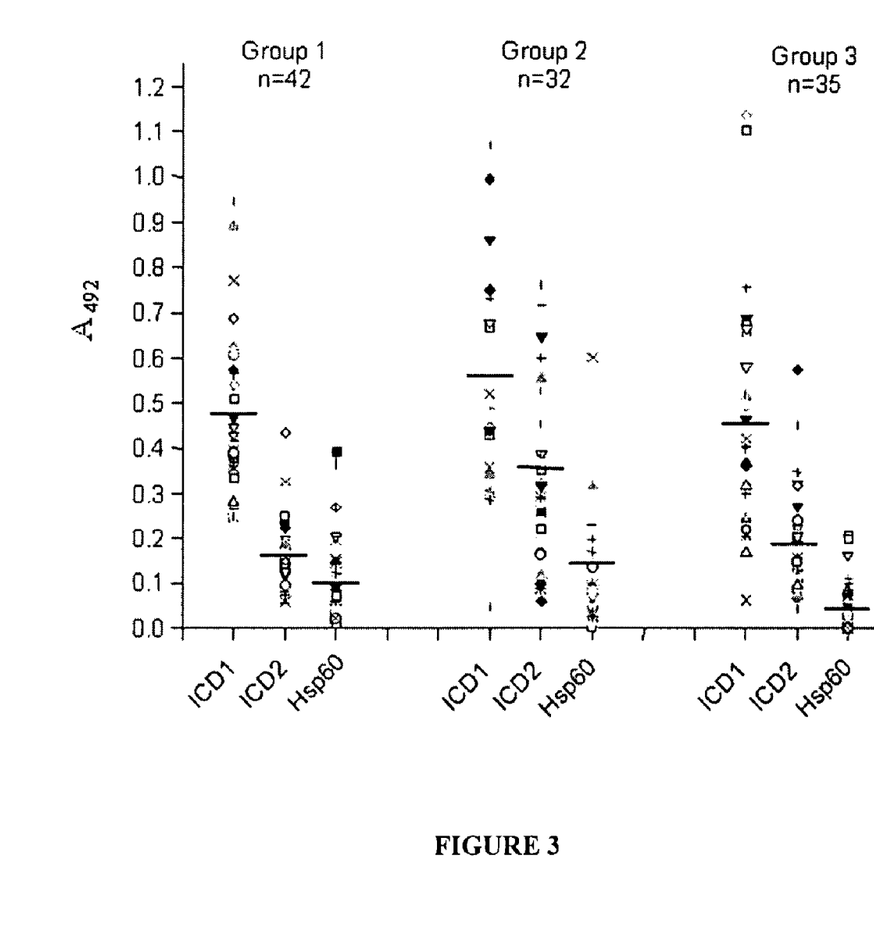
FIG. 3 depicts absorbance values at 492 nm showing that M.tb ICDs are more immunogenic than HSP 60 in accordance with one embodiment of the present invention.

We compared the immunogenicity of ICDs over HSP 60. Humoral response to HSP 60 in all the three categories of TB patients was tested and compared with those to ICDs (FIG. 3). The data clearly indicate that the mean reactivity (represented by the horizontal bands in FIG. 3) of HSP 60 in all the classes of patient sera was much lower than either ICD-1 or ICD-2 (FIG. 3). Thus ICDs are immunodominant and serologically more sensitive than HSP 60. The mean values for ICD-1 in the Groups 1, 2 and 3 were 0.481, 0.565 and 0.457 respectively, while those for ICD-2 were 0.165, 0.362 and 0.188 respectively. It is therefore apparent that ICD-1 elicited a stronger response in all the three categories of patients tested than ICD-2. The data also confirm the discriminatory power of ICD-2 for relapsed case as compared to other categories:

Immunospecificity of M.tb ICDs

Figure 4A:
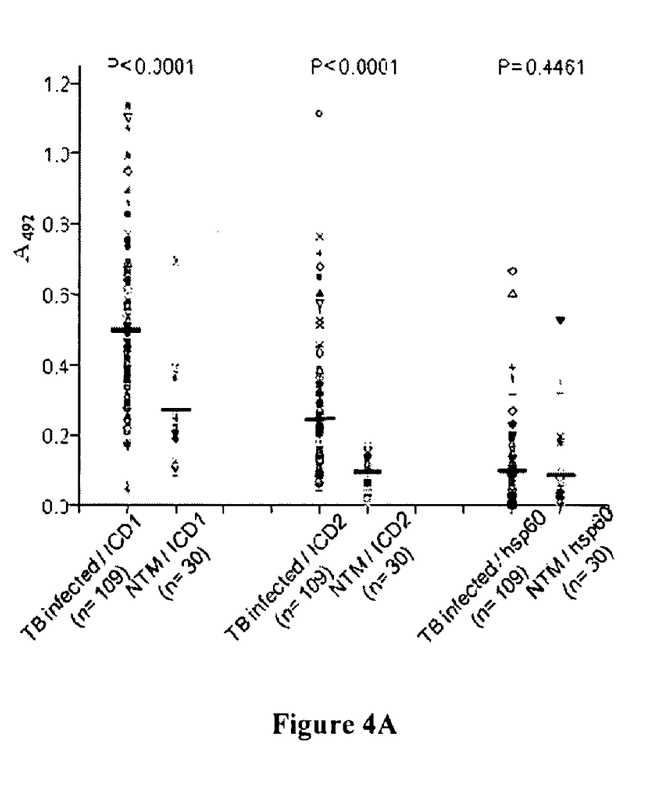
FIG. 4 depicts absorbance values at 492 nm showing that M.tb ICDs could significantly distinguish TB-infected sera from NTMs and non-TB patient sera in accordance with one embodiment of the present invention.
Figure 4B:
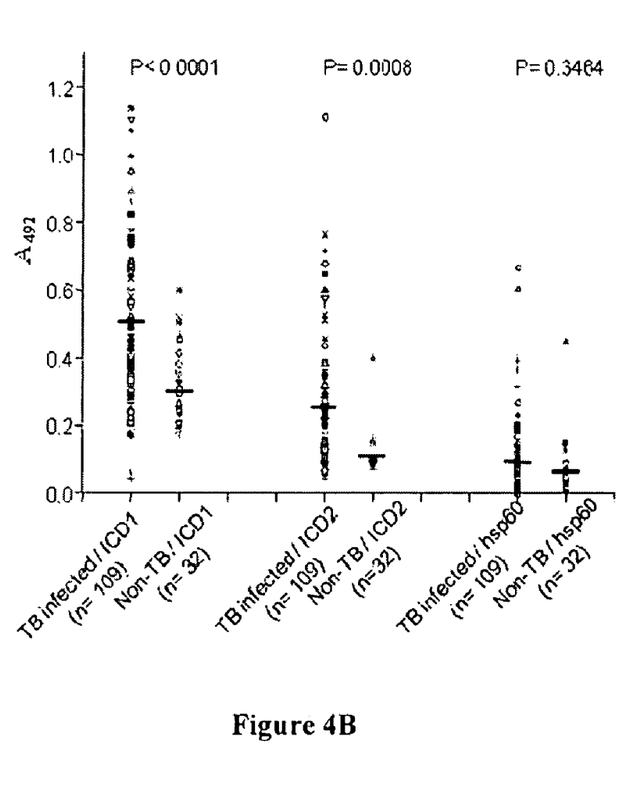

The potential of M.tb ICDs to specifically distinguish between TB, NTMs and non-TB patient sera (those essentially culture negative for acid fast bacteria but harboring other pathogens) was tested by examining the cross-reactivity of the recombinant proteins with NTMs and non-TB patient sera. Thirty NTMs and thirty two non-TB patient sera were tested for their immunogenic response against M.tb ICD-1, M.tb ICD-2 and HSP 60. The data were statistically analyzed to check if ICDs could significantly distinguish between TB infected patients and NTMs or non-TB patients. FIGS. 4A and 4B show that ICDs could significantly distinguish TB-infected sera from NTMs ($p<0.0001$) and non-TB ($p<0.0001$ for ICD-1 and $p=0.0008$ for ICD-2), thus ruling out any cross reactivity with non-tuberculous mycobacteria and other bacterial pathogen tested. HSP 60 appeared to react more broadly to the population under study and could not differentiate between TB infections and NTMs ($p=0.4461$) or non-TB ($p=0.3464$) significantly. This was apparent by calculating the average reactivity for each group; infected, NTMs and non-TB; where reactivity to HSP 60 remain almost the same (FIGS. 4A and 4B). This is in contrast to mean humoral response to ICD-1 and ICD-2, where a distinctly higher response was seen in TB infected sera as compared to NTMs or non-TB cases.

DISCUSSION

The main objective of our study was to evaluate M.tb ICD-1 and M.tb ICD-2 in terms of their immune features as compared to the control antigens HSP 60 and PPD that are frequently used for diagnosis of tuberculosis. ICDs serve as marker of autolysis (16, 17) and are amongst the secretory proteins released during late logarithmic phase. While earlier efforts have pointed to the antigenic potential of M.tb ICDs (17), the present study is the first systematic investigation of their potential as an immune marker.

Figure 2:
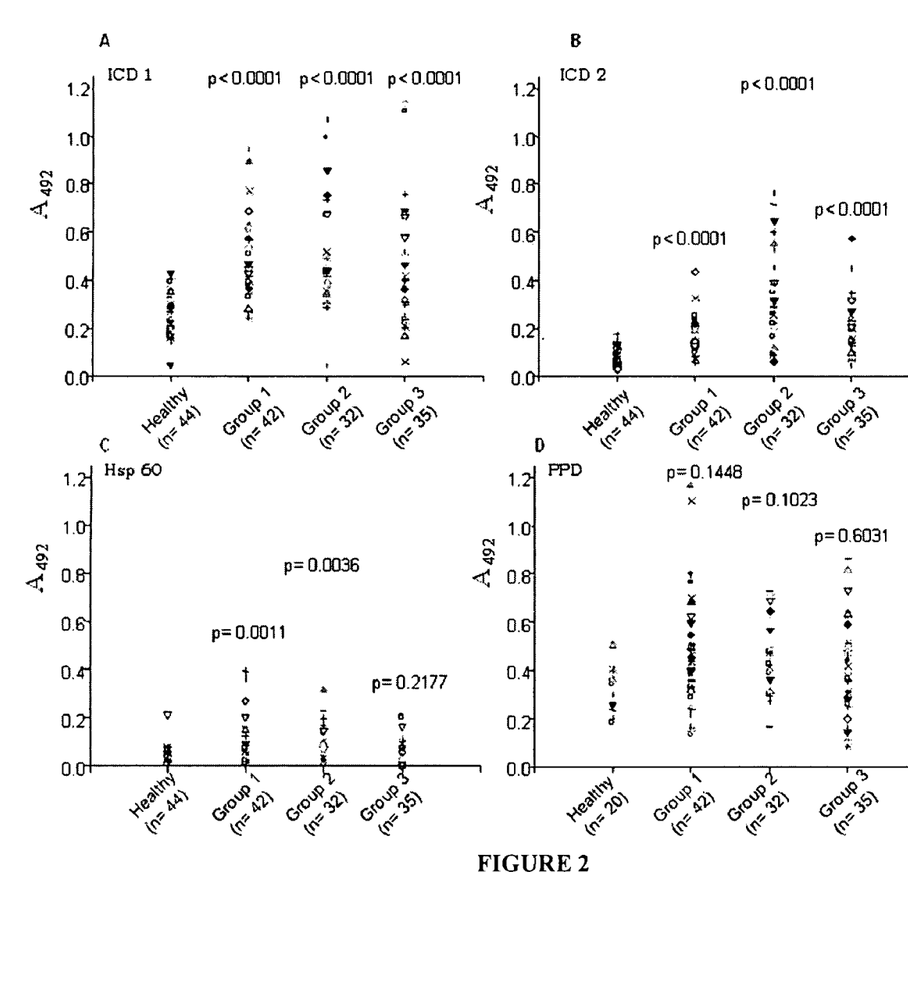
FIG. 2 depicts absorbance values at 492 nm for M.tb ICD-1 and ICD-2 showing high B-cell reactivity to sera from TB infected patients from different groups as opposed to BCG vaccinated healthy controls in accordance with one embodiment of the present invention.

The cases of tuberculosis were identified and enrolled based on their history of treatment as fresh infections, relapsed cases and extrapulmonary infections. The categorization of patients largely depended upon the treatment history dictated by the patients or their family members. As evident from FIG. 2, there is little doubt about the ability of either M.tb ICD-1 or M.tb ICD-2 to elicit a strong B-cell response, irrespective of patient category. When compared to M.tb ICD-2, M.tb ICD-1 was more antigenic (FIGS. 2 and 3). It would be interesting to explore this disparity. A comparative analysis of ELISA reactivities amongst different categories of patients for M.tb ICDs (FIGS. 2A and 2B) revealed higher reactivity in the Group 2 as compared to fresh (Group 1) and extrapulmonary (Group 3) infections. More specifically, the antigenic response in this category of patients to ICD 2 was significantly higher than that in Group 1 and Group 3. Since, these patients had undergone treatment earlier, high number of autolysed infected macrophages and autolysed pathogens could possibly explain the comparative high antibody response against M.tb ICDs in this category. Drugs, like isoniazid, are known to affect the cell envelope architecture of *mycobacteria* and hence the increase in the production of the secreted proteins (22).

Comparative immunoreactivity of M.tb ICD-1, M.tb ICD-2 and HSP 60 clearly indicates that the antigenic distinction between healthy and tuberculosis patients is statistically significant for both M.tb ICD-1 and M.tb ICD-2 ($p<0.0001$), but not quite so for Hsp60 ($p=0.0645$). Earlier reports have shown cross-reactive epitopes between microbial HSP60/65 and human HSP60, which often serve as autoimmune targets in conditions like atherosclerosis (19). This probably could explain the broader reactivity of HSP 60 to healthy and infected sera. Since negligible antibody responses were obtained in the BCG-vaccinated healthy control group as compared to TB infected patients and a statistically significant difference in the immunoreactivity between infected and healthy sera was observed, it can be argued that M.tb ICD-1 and M.tb ICD-2 can be used for diagnosis of *M. tuberculosis* infection even in areas where BCG vaccination is routinely followed. The poor performance of PPD can be attributed to its non-specific immune reaction in BCG-vaccinated healthy controls. Interestingly, the extrapulmonary TB cases (Group 3) in the study population did not show any significant humoral response to HSP 60 to distinguish them from healthy controls. On the other hand, Group 3 patients mounted a very significant B-cell response to ICD-1 and ICD-2, separating them from BCG vaccinated healthy controls.

Immunodominance is a parameter that we defined to compare the antibody titers against the tested proteins, i.e., ICD-1, ICD-2 and HSP 60, in the patient sera. Our data clearly showed that ICD-1 was most antigenic and mounted a very strong B-cell response in all the patient categories, followed by ICD-2 and HSP 60 (FIG. 3). Having shown that M.tb ICDs elicit a B-cell response much higher than HSP 60, we checked for immune specificity of these proteins. Cross-reaction with sera of NTMs and non-TB patient is one of the critical parameters that needed to be checked before establishing any antigenic marker for possible serological studies in M.tb. *Mycobacterium tuberculosis* complex, including *M. bovis* and *M. africanum*, is responsible for more illness worldwide than any other bacteria. However, there are more than 82 recognized species of *mycobacteria* that occasionaly infect mammalian hosts. These are referred to as nontuberculous mycobacteria (NTM). NTMs are omnipresent in the environment and most species are either non-pathogenic for humans or are rarely associated with disease, except a few like *M. avium*, that are opportunistic pathogens, more frequently associated with immunocompromised patients (23, 24). The clinical significance of many NTM remains unclear, however it is important to check the crossreactivity of M.tb antigens with this group of mycobacteria. Our experiments could establish that M.tb ICDs do not cross-react with either NTMs or non-TB patient sera (FIGS. 4A and 4B).

The existing diagnostic tests for tuberculosis, even to this day, largely depends on tuberculin skin test and staining and culture techniques. These methods are slow, cumbersome and lack sensitivity and specificity in BCG vaccinated cases. As more and more recombinant antigens are being tested (25-31) serological methods are likely to be favoured over others. ELISA per se is unlikely to replace the current tuberculosis diagnosis, however in combination or parallel with other rapid PCR based diagnostic techniques, ELISA can largely improve the accuracy and rapidity of tuberculosis diagnosis for an effective disease management. Our data, for the first time, reveal the antigenic potential of recombinant M.tb ICD-1 and also present a systematic study on immunogenicity of recombinant M.tb ICD-2. M.tb ICD-1 and M.tb ICD-2 can be further analyzed for their pathogen specific antigenic epitopes. Given their important role in the energy cycle, we are currently evaluating these two enzymes of M.tb as possible drug targets. That such important enzymes can also have strong antigenic attributes which enable them to significantly discriminate between BCG-vaccinated healthy controls and TB patients and at the same time TB from other pathogenic infections is a very exciting and novel proposition possibly pointing to their immunomodulatory function.

ACKNOWLEDGEMENTS

This project was supported by research grants from the Council of Scientific and Industrial Research (CSIR) and Department of Biotechnology, Government of India to SEH. SB thanks the CSIR for Senior Research Fellowship. We thank Dr. Shekhar Mande for providing purified recombinant M.tb HSP 65/GroEL.

REFERENCES

1. Dye, C., Scheele, S., Dolin, P., Pathania, V., & Raviglione, M. C. (1999) *JAMA*, 282, 677-686.
2. Bloom, B. R., & Murray, C. J. L. (1992) *Science*. 257, 1055-1064.
3. Chakhaiyar, P. & Hasnain, S., E. (2004) *Medical Principles and Practice*. (In Press).
4. Helmuth, L. (2000) *Science*. 289, 1123-1125.
5. Dye, C., Espinal, M. A., Watt, C. J., Mbiaga, C., & Williams, B. G. (2002) *J. Infect. Dis.* 185, 1197-1202.
6. Siddiqi, N., Shamim, M., Hussain, S., Choudhary, R. K., Ahmed, N., Prachee, Banerjee, S., Savithri, G. R., Alam, M., Pathak, N., et al. (2002) *Antimicrob. Agents Chemother*. 46, 443-450.
7. Ahmed, N., Caviedes, L., Alam, M., Rao, K. R., Sangal, V., Sheen, P., Gilman, R. H., & Hasnain, S. E. (2003) *J. Clin. Microbiol*. 41, 1712-1716.
8. Ahmed, N., Alam, M., RajenderRao, K., Kauser, F., Ashok Kumar, N., Qazi, N., N., Sangal, V., Sharma, V., D., Das, R., Katoch, V., M., et al (2004). *J. Clin. Microbiol*. (In Press).
9. Roche, P. W., Triccas, J A., Avery, D. T., Fifis, T., Billman-Jacobe, H., & Britton, W. J. (1994) *J. Infect. Dis.* 170, 1326-1330.
10. Laidlaw, M. (1989) In *Practical Medical Microbiology*, eds. Colle, J. G., Duguid, J. P., Fraser, A. G., & Marimon, B, P. (New York, Churchill Livingstone), pp. 399-416.
11. Horwitz, M. A., Lee, B. W., Dillon, B. J., & Harth, G. (1995) *Proc. Natl. Acad. Sci. USA* 92, 1530-1534.
12. Mustafa, A. S. (2002) *Mol. Immunol*. 39, 113-119.
13. Louise, R., Skjot, V., Agger, E. M., & Andersen, P. (2001) *Scand. J. Infect. Dis.* 33, 643-647.
14. Trajkovic, V., Natarajan, K., & Sharma, P. (2004) *Microbes Infect*. 6, 513-519.
15. Mori, T., Sakatani, M., Yamagishi, F., Takashima, T., Kawabe, Y., Nagao, K., Shigeto, E., Harada, N., Mitarai, S., Okada, M., et al (2004) *Am. J. Respir. Cit. Care Med.* 0, 200402179-0 (In Press).
16. Anderson, P., Askgaard. D., Ljungqvist, L., Bennedsen, J., & Heron I. (1991) *Infect. Immun.* 59, 1905-1910.
17. Ohman, R., & Ridell, M. (1996) *Tuber. Lung Dis.* 77, 454-461.
18. Florio, W., Bottai, D., Batoni, G., Esin, S., Pardini, M., Maisetta, G., & Campa, M. (2002) *Clin. Diagn. Lab. Immunol.* 9, 846-851.
19. Perschinka, H., Mayr, M., Millonig, G., Mayerl, C., van der Zee, R., Morrison, S. G., Morrison, R. P., Xu, Q., & Wick, G. (2003) *Arterioscler Thromb Vasc Biol*. 23, 1060-1065.
20. Bradford, M. M. (1976) *Analyt. Biochem.* 72, 248-252.
21. Saiman, L. (2004) *Paediatr. Respir. Rev.* 221-3.
22. Bardou, F., Quemard, A., Dupont, M. A., Horn, C., Marchal, G., & Daffe, M. (1996) *Antimicrob. Agents Chemother.* 40, 2459-2467.
23. Shiratsuch, H., & Basson, M. D. (2003) *Am. J. Surg.* 186, 547-551.
24. Hadad, D. J., Palaci, M., Pignatari, A. C., Lewi, D. S., Machado, M. A., Telles, M. A., Martins, M. C., Ueki, S. Y., Vasconcelos, G. M., Palhares, M. C. (2004) *Epidemiol. Infect*. 132, 151-155.
25. Choudhary, R. K. Mukhopadhyay, S., Chakhaiyar, P., Sharma, N., Murthy, K. J. R., Katoch, V. M., & Hasnain, S. E. (2003) *Infection Immunity*. 71, 6338-6343.
26. Ramalingam, B., UmaDevi, K. R., & Raja, A. (2003) *Scand. J. Infect. Dis.* 35, 234-239.
27. Brusasca, P. N., Peters, R. L., Motzel, S. L., Klein, H. J., & Gennaro M. L. (2003) *Comp. Med.* 53, 165-172.
28. Maekura, R., Kohno, H., Hirotani, A., Okuda, Y., Ito, M., Ogura, T., & Yano, I. (2003) *J. Clin. Microbiol.* 41, 1322-1325.
29. Perkins, M. D., Conde, M. B., Martins, M., & Kritski, A. L. (2003) *Chest* 123, 107-112.
30. Maekura, R., Okuda, Y., Nakagawa, M., Hiraga, T., Yokota, S., Ito, M., Yano, I., Kohno, H., Wada M., Abe, C., et al. (2001) *J. Clin. Microbiol.* 39, 3603-3608.
31. Chakhaiyar, P., Nagalakshmi, Y., Aruna, B., Murthy, K., J., R, Katoch, V., M., & Hasnain, S., E. (2004) *J. Infect. Dis.* (In Press).

LEGENDS

Table 1: PCR primers and thermal cycle parameters for amplification of M.tb ICD-1 and ICD-2

FIG. 1: Affinity purification of M.tb ICD-1 and M.tb ICD-2. Histidine-tagged recombinant protein was purified by nickel column chromatography under native condition and stained with Coomassie Blue following electrophoresis on 10% SDS polyacrylamide gels. The different lanes are: lanes 1 and 2: M.tb ICD-2; lane M: protein molecular size markers (200 kDa, 116 kDa, 97 kDa, 66 kDa, 45 kDa, 31 kDa and 21.5 kDa); lanes 3 and 4: M.tb ICD-1.

FIG. 2: M.tb ICD-1 and ICD-2 show high B-cell reactivity to sera from TB infected patients from different groups as opposed to BCG vaccinated healthy controls. The humoral immune responses directed against the recombinant proteins, M.tb ICD-1 (2A) and M.tb ICD-2 (2B) and control antigens HSP 60 (2C) and PPD (2D) were compared between different categories of patients and healthy controls. Group 1: fresh infections, Group 2: relapsed infection and Group 3: extrapulmonary TB. The respective sample numbers and p values are shown.

FIG. 3: M.tb ICDs are more immunogenic than HSP 60. The ELISA reactivity to M.tb ICD-1, M.tb ICD-2 and control antigen HSP 60 was compared in different patient groups.

Horizontal bands represent the mean reactivity or average levels of humoral response in each category.

FIG. 4: M.tb ICDs could significantly distinguish TB-infected sera from NTMs and non-TB patient sera. Recombinant M.tb ICD-1 and M.tb ICD-2 as well as HSP 60 were tested against sera of NTM (4A) and non-tuberculosis patients (4B). The respective humoral responses were compared to TB-infected sera, the p values for which are given in the figures. HSP 60 could not distinguish TB-infected patient from either NTM or non-TB significantly. Horizontal bands represent the mean reactivity in each category.

TABLE 1

PCR primers and termal cycle parameters for amplification of M.tb ICD-1 and ICD-2

| Seq. ID | Primers | Sequence | PCR Parameters | Amplicon Size |
|---|---|---|---|---|
| 1 | M.tb icd-1FP | ggatccATGTCCAACGCA CCCAAGATA | 94° C. for 2' (35 Cycles) 94° C. for 30" 50° C. for 1' 72° C. for 3' 72° C. for 7' | ~1.2 Kb |
| 2 | M.tb icd-1RP | aagcttCTAATTGGCCAG CTCCTTTTC | | |
| 3 | M.tb icd-2FP | AGCTTggatccATGAGCG CCGAACAGCC | 94° C. for 2' (10 Cycles) 94° C. for 30" 50° C. for 30" 72° C. for 3.30' (25 cycles) 94° C. for 30" 58° C. for 30" 72° C. for 3.30' 72° C. for 7' | ~2.23 Kb |
| 4 | M.tb icd-2RP | CATGGaagcttTCAGCCT TGGACAGCCT | | |

The invention claimed is:

1. A method of distinguishing subjects with freshly infected, relapsed and extra-pulmonary tuberculosis from healthy BCG-vaccinated subjects, said method comprising steps of:
   a) identifying antibody immunoreactivity in the subjects to *M. tuberculosis* Iso Citrate Dehydrogenase-1 (ICD-1) and Iso Citrate Dehydrogenase-2 (ICD-2), and
   b) distinguishing the subjects based on antibody response, wherein subjects with freshly infected, relapsed and extrapulmonary tuberculosis elicit a higher response to both *M. tuberculosis* ICD-1 and *M. tuberculosis* ICD-2 as compared to healthy BCG-vaccinated subjects.

2. A method as claimed in claim 1, wherein the subject is mammal including human.

3. A method as claimed in claim 1, wherein the antibodies are detected using enzyme linked immunosorbent assays (ELISA).

* * * * *